(12) United States Patent
Kenney et al.

(10) Patent No.: US 6,615,663 B2
(45) Date of Patent: Sep. 9, 2003

(54) METHOD AND APPARATUS FOR ACOUSTIC SENSING

(75) Inventors: Martin J. Kenney, Index, WA (US); William L. Lowry, Woodinville, WA (US)

(73) Assignee: Ultrasonic Arrays, Inc., Woodinville, WA (US)

( * ) Notice: Subject to any disclaimer, the term of this patent is extended or adjusted under 35 U.S.C. 154(b) by 0 days.

(21) Appl. No.: 09/771,342

(22) Filed: Jan. 26, 2001

(65) Prior Publication Data

US 2001/0035050 A1 Nov. 1, 2001

Related U.S. Application Data
(60) Provisional application No. 60/178,692, filed on Jan. 28, 2000.

(51) Int. Cl.[7] ............................................. G01N 29/04
(52) U.S. Cl. .............................. 73/632; 73/600; 73/644
(58) Field of Search ........................ 73/599, 600, 618, 73/629, 630, 632, 644

(56) References Cited

U.S. PATENT DOCUMENTS 4,594,897 A  *  6/1986  Bantz ........................... 73/600
5,824,908 A  * 10/1998  Schindel et al. ............... 73/632
6,367,330 B1 *  4/2002  Schafer ........................ 73/600

* cited by examiner

*Primary Examiner*—John E. Chapman
(74) *Attorney, Agent, or Firm*—Seed IP Law Group PLLC

(57) ABSTRACT

An acoustic sensing system to measure an interior characteristic of an object, for example, density, the presence of defects, or bond integrity (of a laminated object). The system includes a first set of acoustic transducers acting as transmitters for transmitting acoustic wave energy at a single frequency, which acoustic wave energy interacts with the object in a sensing region to provide transmitted, scattered, and reflected wave energy. A transmitter mounting mechanism allows the transmitters to be positioned in such a way that acoustic energy reflected from the object sets up a reverberation between the transmitter and the object. A second set of acoustic transducers acting as receivers of acoustic wave energy is positioned opposite the transmitters in such a way that acoustic waves passing through the object are coupled to the receivers. A second mounting mechanism allows the receivers to be similarly positioned such that acoustic energy passing through the object sets up a reverberation between the receiver and the object. A processor is connected to generate electrical control signals to the transmitter and to receive electrical signals from the receiver. The processor is operable to adjust the frequency of the electrical control signals to the transmitter in order to maintain a maximum of reverberation, and therefore a maximum of received signal at the receiver.

10 Claims, 5 Drawing Sheets

Divisor = 256−(n+92)    where n = frequency step number
freq = (5529600 + divisor*2)/divisor

| n | divisor | freq | Delta |  | n | divisor | freq | Delta |
|---|---|---|---|---|---|---|---|---|
| 0 | 164 | 33719.07 | | | 51 | 113 | 48936.51 | 429.2501 |
| 1 | 163 | 33925.93 | 206.8532 | | 52 | 112 | 49373.43 | 436.9153 |
| 2 | 162 | 34135.33 | 209.407 | | 53 | 111 | 49818.22 | 444.7876 |
| 3 | 161 | 34347.34 | 212.0083 | | 54 | 110 | 50271.09 | 452.8747 |
| 4 | 160 | 34562 | 214.6584 | | 55 | 109 | 50732.28 | 461.1843 |
| 5 | 159 | 34779.36 | 217.3585 | | 56 | 108 | 51202 | 469.7248 |
| 6 | 158 | 34999.47 | 220.1099 | | 57 | 107 | 51680.5 | 478.5047 |
| 7 | 157 | 35222.38 | 222.9138 | | 58 | 106 | 52168.04 | 487.5331 |
| 8 | 156 | 35448.15 | 225.7717 | | 59 | 105 | 52664.86 | 496.8194 |
| 9 | 155 | 35676.84 | 228.6849 | | 60 | 104 | 53171.23 | 506.3736 |
| 10 | 154 | 35908.49 | 231.6548 | | 61 | 103 | 53687.44 | 516.2061 |
| 11 | 153 | 36143.18 | 234.683 | | 62 | 102 | 54213.76 | 526.3278 |
| 12 | 152 | 36380.95 | 237.7709 | | 63 | 101 | 54750.51 | 536.7501 |
| 13 | 151 | 36621.87 | 240.9202 | | 64 | 100 | 55298 | 547.4851 |
| 14 | 150 | 36866 | 244.1325 | | 65 | 99 | 55856.55 | 558.5455 |
| 15 | 149 | 37113.41 | 247.4094 | | 66 | 98 | 56426.49 | 569.9443 |
| 16 | 148 | 37364.16 | 250.7528 | | 67 | 97 | 57008.19 | 581.6958 |
| 17 | 147 | 37618.33 | 254.1644 | | 68 | 96 | 57602 | 593.8144 |
| 18 | 146 | 37875.97 | 257.6461 | | 69 | 95 | 58208.32 | 606.3158 |
| 19 | 145 | 38137.17 | 261.1998 | | 70 | 94 | 58827.53 | 619.2161 |
| 20 | 144 | 38402 | 264.8276 | | 71 | 93 | 59460.06 | 632.5326 |
| 21 | 143 | 38670.53 | 268.5315 | | 72 | 92 | 60106.35 | 646.2833 |
| 22 | 142 | 38942.85 | 272.3136 | | 73 | 91 | 60766.84 | 660.4873 |
| 23 | 141 | 39219.02 | 276.1762 | | 74 | 90 | 61442 | 675.1648 |
| 24 | 140 | 39499.14 | 280.1216 | | 75 | 89 | 62132.34 | 690.3371 |
| 25 | 139 | 39783.29 | 284.1521 | | 76 | 88 | 62838.36 | 706.0266 |
| 26 | 138 | 40071.57 | 288.2703 | | 77 | 87 | 63560.62 | 722.2571 |
| 27 | 137 | 40364.04 | 292.4786 | | 78 | 86 | 64299.67 | 739.0537 |
| 28 | 136 | 40660.82 | 296.7797 | | 79 | 85 | 65056.12 | 756.4432 |
| 29 | 135 | 40962 | 301.1765 | | 80 | 84 | 65830.57 | 774.4538 |
| 30 | 134 | 41267.67 | 305.6716 | | 81 | 83 | 66623.69 | 793.1153 |
| 31 | 133 | 41577.94 | 310.2682 | | 82 | 82 | 67436.15 | 812.4596 |
| 32 | 132 | 41892.91 | 314.9692 | | 83 | 81 | 68268.67 | 832.5203 |
| 33 | 131 | 42212.69 | 319.7779 | | 84 | 80 | 69122 | 853.3333 |
| 34 | 130 | 42537.38 | 324.6976 | | 85 | 79 | 69996.94 | 874.9367 |
| 35 | 129 | 42867.12 | 329.7317 | | 86 | 78 | 70894.31 | 897.371 |
| 36 | 128 | 43202 | 334.8837 | | 87 | 77 | 71814.99 | 920.6793 |
| 37 | 127 | 43542.16 | 340.1575 | | 88 | 76 | 72759.89 | 944.9077 |
| 38 | 126 | 43887.71 | 345.5568 | | 89 | 75 | 73730 | 970.1053 |
| 39 | 125 | 44238.8 | 351.0857 | | 90 | 74 | 74726.32 | 996.3243 |
| 40 | 124 | 44595.55 | 356.7484 | | 91 | 73 | 75749.95 | 1023.621 |
| 41 | 123 | 44958.1 | 362.5492 | | 92 | 72 | 76802 | 1052.055 |
| 42 | 122 | 45326.59 | 368.4926 | | 93 | 71 | 77883.69 | 1081.69 |
| 43 | 121 | 45701.17 | 374.5834 | | 94 | 70 | 78996.29 | 1112.596 |
| 44 | 120 | 46082 | 380.8264 | | 95 | 69 | 80141.13 | 1144.845 |
| 45 | 119 | 46469.23 | 387.2269 | | 96 | 68 | 81319.65 | 1178.517 |
| 46 | 118 | 46863.02 | 393.7901 | | 97 | 67 | 82533.34 | 1213.696 |
| 47 | 117 | 47263.54 | 400.5215 | | 98 | 66 | 83783.82 | 1250.475 |
| 48 | 116 | 47670.97 | 407.4271 | | 99 | 65 | 85072.77 | 1288.951 |
| 49 | 115 | 48085.48 | 414.5127 | | | | | |
| 50 | 114 | 48507.26 | 421.7849 | | | | | |

*FIG. 4B*

METHOD AND APPARATUS FOR ACOUSTIC SENSING

CROSS-REFERENCE TO RELATED APPLICATION

This application claims priority from U.S. provisional application No. 60/178,692, filed Jan. 28, 2000, entitled METHOD AND APPARATUS FOR ACOUSTIC SENSING.

TECHNICAL FIELD

The present invention relates to systems for ultrasonic inspection of the interior of an object.

BACKGROUND OF THE INVENTION

Acoustic sensing devices, such as ultrasonic inspection equipment, are used in inspecting the interiors of a variety of objects, including the human body, the area around a weld, and manufactured products such as wood-based panels. The performance of an ultrasonic inspection device is often limited by its ability to couple ultrasonic energy into the object to be inspected. When the ultrasonic waves travelling in air reach a solid surface, much of the energy is reflected away. This reflected energy is then not available to interact with the interior of the object, and it cannot contribute to a measurement of its internal properties. In some applications, placing the ultrasonic transmitter in hard physical contact with the object to be measured can solve the problem. In other applications, the coupling is improved by creating a liquid path between the transmitter and the object. However, use of these techniques is not always possible. It is often desirable to minimize or eliminate contact between the transducer and the object, leaving air-coupled transducers as the only possibility. Therefore, there is a need for an ultrasonic inspection system capable of increasing the energy coupled via air from a transmitter into a solid object and on to a receiver.

One method of increasing the energy coupled into the object and on to a receiver is to carefully control the positioning of the transducers relative to the object. The ideal positioning will depend on characteristics of the acoustic energy, notably the wavelength. The wavelength of an acoustic wave in air will vary with the physical properties of the air, including its temperature, humidity, and pressure. Therefore, there is a further need for an improved air-coupling system that is not affected by the properties of air. Finally, the application of the system may be to the processing of a moving object. Therefore, there is a further need for a method that does not require repeated measurements at the same location.

SUMMARY OF THE INVENTION

The disclosed embodiments of the present invention provide a means of increasing the effective coupling of ultrasonic energy from a transmitter to a solid object, and from the solid object to a receiver, using air as the coupling medium. The present invention further provides an air-coupled system that is not affected by changing properties of the air.

To achieve the foregoing, a method for increasing the coupling in an ultrasonic inspection system is disclosed that incorporates at least one pair of opposed transducers. One transducer in the pair acts as a transmitter, the other as a receiver. The vibrating face of the transmitter is positioned parallel to the surface of the object to be inspected. In this way, acoustic wave energy that is reflected from the object will travel back to the face of the transducer and be reflected once again to the object. The acoustic energy coupled into the object then travels through the object, interacting with its interior. It emerges from the far surface of the object, where the receive transducer is again positioned parallel to the surface of the object.

Because the acoustic energy exists as a wave, the energy reflected at a surface may either add to or subtract from the continuing energy emanating from the surface. When the distance between transducer and object equals a multiple of one-half of the wavelength of the acoustic signal, the reflected energy will add to the continuing energy. Under these circumstances, the space between the transducer face and the object will act as a reverberation chamber; the amount of acoustic wave energy will increase to a peak value. Therefore, the mounting apparatus for the transducers allows them to be initially positioned at a distance from the surface of the object of approximately one-half the wavelength. A processor is used to adjust the frequency of the transmitted signal so that the spacing will in fact be one-half the wavelength of the acoustic wave energy.

In accordance with the disclosed embodiments of the present invention, an acoustic sensing method is provided that includes generating an initial acoustic energy wave or set of acoustic energy waves at a nominal frequency and successive acoustic energy waves or sets of acoustic energy waves through an object. Each successive acoustic energy wave or set of successive acoustic energy waves is generated at a different frequency than the previous acoustic energy wave. The method further includes sensing the initial and successive acoustic energy waves from the object and determining the frequency of the sensed acoustic energy wave having the highest energy level, then changing the nominal frequency to the determined frequency.

In accordance with another aspect of the invention, the successive frequencies are changed both up and down by an incremental value, and then changed again both up and down by a second incremental value. Ideally, the second incremental value is a multiple of the first incremental value.

In accordance with another aspect of the disclosed embodiments of the present invention, an ultrasonic examination system for examining an object is provided. The system includes a microprocessor configured to generate frequency signals; a first transducer configured to receive the frequency signals and adapted to generate acoustic energy waves into the objects; a second transducer adapted to receive acoustic energy waves from the object and to generate corresponding energy value signals to the microprocessor, where the microprocessor is configured to adjust the frequency signals in response to the energy value signals to be at the frequency associated with the highest energy value signal.

In accordance with another aspect of the present invention, a method for acoustic sensing of an object in a computer-controlled system is provided. The method includes performing a plurality of acoustic energy measurements of the object at a nominal frequency and then at different successive frequencies; determining the measured acoustic frequency having the highest acoustic energy, and changing the nominal frequency to the determined frequency. Ideally, the method includes repeatedly performing the plurality of acoustic measurements and determinations.

BRIEF DESCRIPTION OF THE DRAWINGS

FIGS. 4A and 4B are a graph of a frequency curve plotted over incremental steps and an associated table.

DETAILED DESCRIPTION OF THE INVENTION

Figure 1:
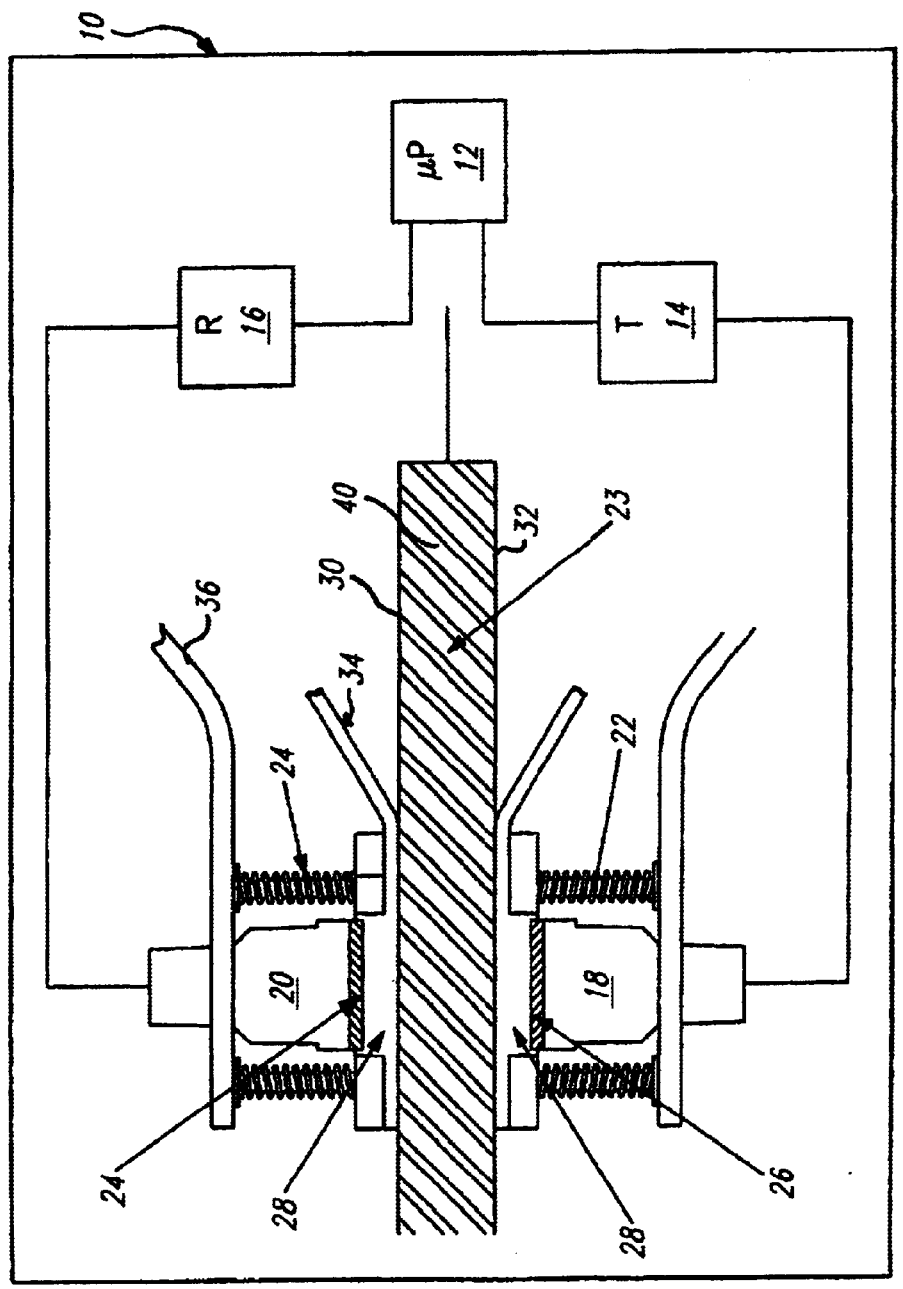
FIG. 1 is a partial cross-sectional side view of the system described herein.
Figure 2:
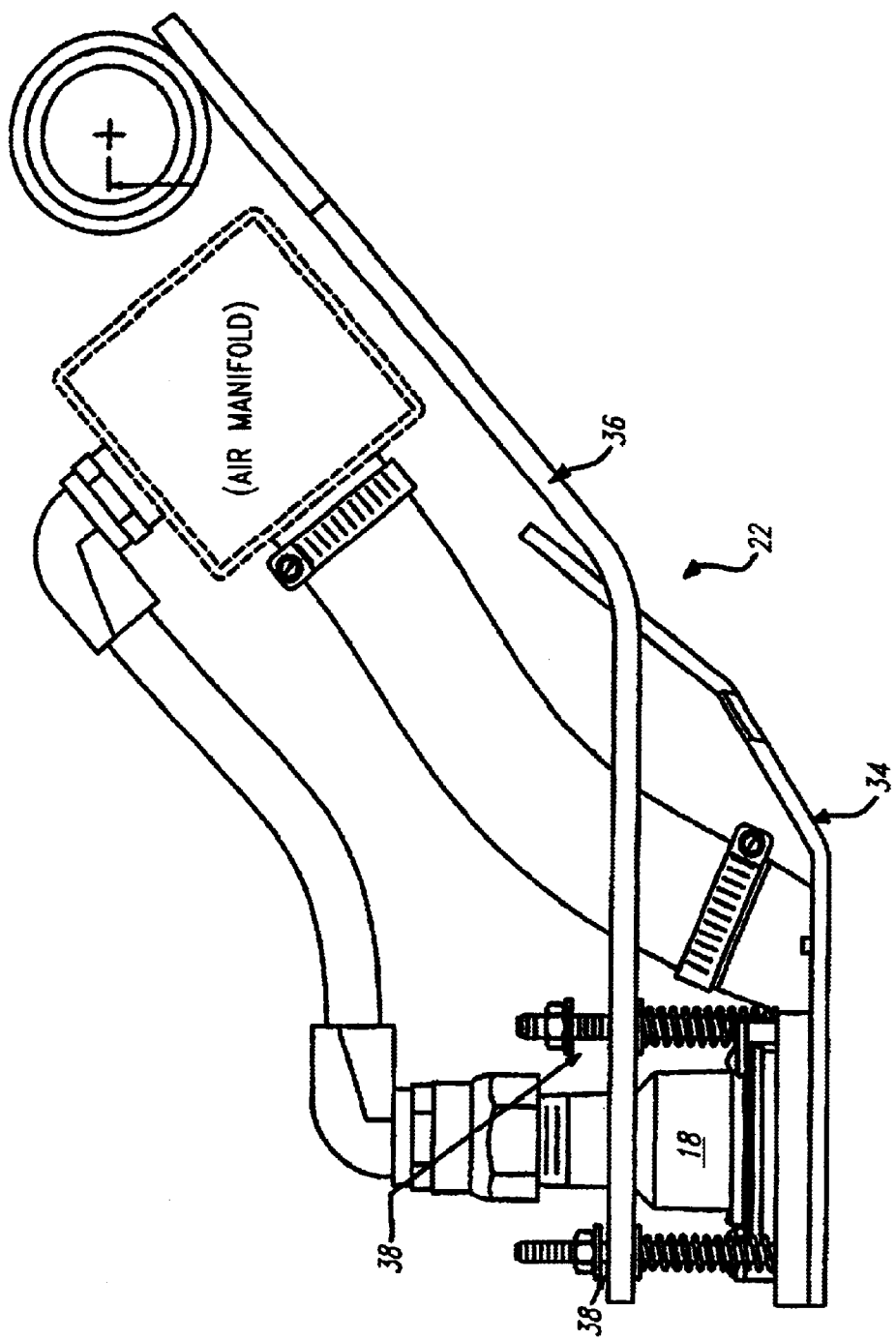
FIG. 2 is a side view of a mounting apparatus formed in accordance with the present invention.

Referring initially to FIGS. 1 and 2, shown therein is an ultrasonic measurement system 10 that includes a controller or microprocessor 12, transmitter electronics 14, receiver electronics 16, and ultrasonic transducers acting as a transmitter 18 and a receiver 20 mounted opposite each other. A mounting apparatus 22 and 24 for the transmitter 18 and receiver 20, respectively, maintain the transducers approximately parallel to the surface of an object 23 whose interior is to be probed. The vibrating faces 24 and 26 of the transmitter and receiver transducers 18 and 20 form reverberation chambers 28 with the top and bottom surfaces 30, 32 of the object 23.

The mounting apparatus 22 is shown in greater detail in FIG. 2, wherein the transmitter 18 is mounted to a foot plate 34 that in turn is attached to a mounting arm 36 by threaded rods 38. The foot plate 34 bears against the object 23 to maintain the transducer 18 a predetermined distance from the top surface 30. The receiver 20 is similarly mounted to an identical apparatus.

The transducers 18 and 20 are readily commercially available and will not be described in detail herein. In a preferred embodiment, the transducers comprise model SC43PS available from Kistler-Morse. The microprocessor 12 is a manufactured component that includes an 8051 microprocessor in one embodiment. The transmitter electronics 14 and the receiver electronics 16 are electronic circuits that reside on a single transceiver card and are configured to process control signals to the transmitter 18 and received signals from the receiver 20, respectively. More particularly, the transmitter electronics 14 receives control signals from the microprocessor 12 and generates pulse signals to the transmitter 18; and the receiver electronics 16 processes signals from the receiver 20 into waveform signals usable by the microprocessor 12.

In operation, upon power up the controller 12 directs the transmitter electronics 14 to generate a signal at a specific nominal frequency. The signal is received at the transmitter transducer 18, and an acoustic wave is generated at the nominal frequency. The acoustic wave builds up in the reverberation chamber 28 adjacent to the transmitter 18. Part of this acoustic wave energy is coupled into the object 23 at its bottom surface 32, interacts with its interior 40, and continues to its top surface 30. At the top surface 30, part of the acoustic wave energy emerges from the object 23 and builds up in the reverberation chamber 28 adjacent to the receiver transducer 20, which converts the acoustic wave into a corresponding electric signal that is sent to the receiver electronics 16 and in turn to the controller 12 as acoustic energy signals. After waiting for this physical process to occur, the controller 12 measures and compares the amplitude of the acoustic energy as reflected in the signals generated by the receiver electronics 16.

In one application, the object 23 is a board, such as a sheet of plywood. The board 23 is continuously moved between the transducers 18 and 20, which measure the acoustic characteristics of the board 23. In another embodiment, a plurality of transducer pairs arranged linearly provide a plurality of acoustic measurements along a transverse or longitudinal direction of the board 23.

Figure 3:
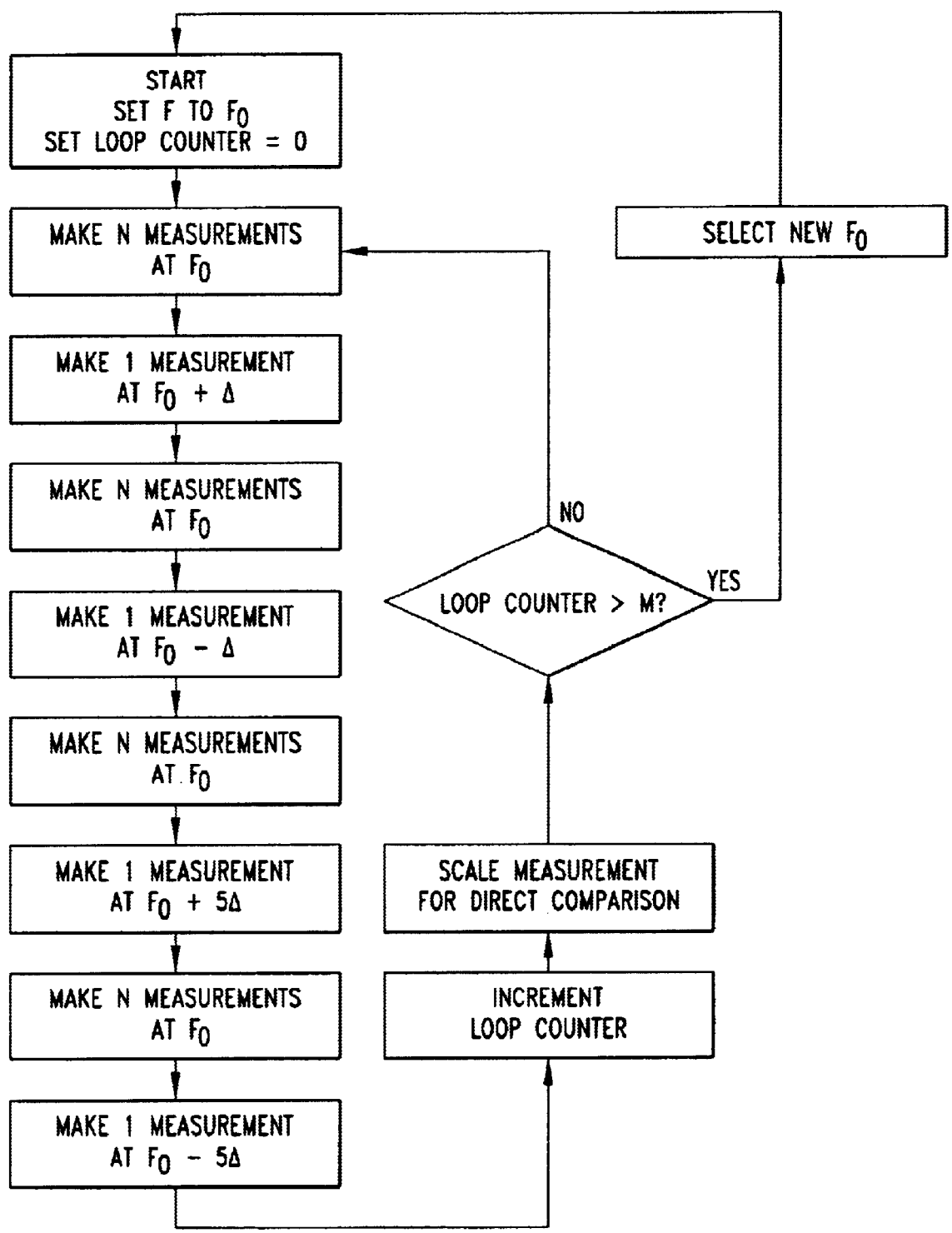
FIG. 3 is a flow chart depicting one method of the present invention.
Figure 4A:
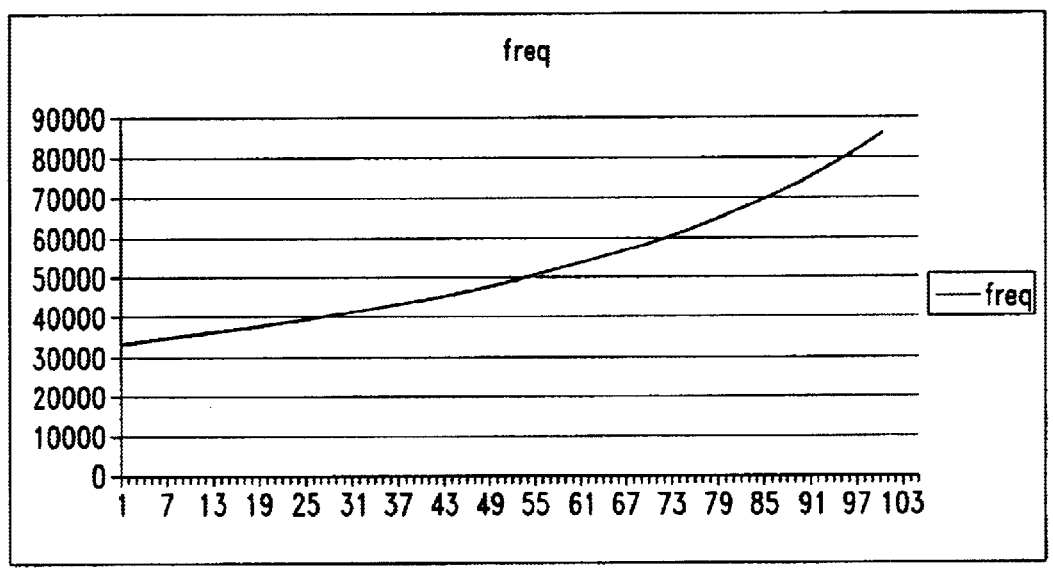

Referring next to FIGS. 3 and 4A–4B, the frequency adaptive scheme of the present invention will be described. The microprocessor 12 begins by sending a control signal to the transmitter electronics 14 that in turn generates an electrical signal at a previously-selected nominal frequency. The transmitter 18 converts the electric signal into an ultrasonic acoustic energy wave that travels from the transmitter 18 through the object 23 and to the receiver 20, and to build up via reverberation in the two reverberation chambers 28. The receiver 20 then converts the acoustic energy into an electrical acoustic energy signal that is received by the receiver electronics 16, which processes the signal through known filter and gain circuits to achieve a waveform of the received acoustic energy that is usable by the microprocessor 12.

The microprocessor 12 then begins a cyclic process to determine if another frequency will generate an increased received acoustic energy, which would indicate that the ½ wavelength condition is not satisfied by the nominal frequency. A measurement is made at the nominal frequency. This is called the reference value. After several such measurements at the nominal frequency, the frequency is increased by a small incremental value; the resulting measurement is called the +1 value. In order for the method to work with a moving object, the frequency is immediately changed back to the nominal value. After several more measurements at the nominal frequency, the frequency is decreased by a small incremental value; the resulting measurement is called the −1 value. In one embodiment the +1 value and the −1 value have the same absolute value. Again, the frequency is immediately changed back to the nominal value.

After several measurements, the frequency is increased by a larger incremental value. For the purpose of illustration, the larger increment can be chosen to be five times the smaller increment, but other multiples will also work. In the embodiment depicted in FIGS. 3, the resulting measurement is called the +5 value. Again, the frequency is immediately changed back to the nominal value. After several measurements, the frequency is decreased by the larger incremental value. The resulting measurement is called the −5 value.

An appropriate mathematical scaling is then used on the measurements to allow direct comparison of the values. For example, each time any measurement is made, the last measured values at the nominal, +1, −1, +5 and −5 frequencies can be added to a running total. The inner loop of the cycle is now complete and begins again.

After a predetermined number of iterations of this inner loop, the processor compares the scaled values of the reference, +1, −1, +5, and −5 measurements. The frequency that generated the largest scaled value is then selected as the reference frequency for the next cycle. The reference frequency is changed, and the process repeats. Ideally, the nominal frequency is changed only when a new object is measured. However nominal frequency adjustments can be made as often as desired.

By way of example, the following description provides an application of the present invention in the field of inspecting internal structures of wood products, such as laminated wood or plywood. FIG. 4A is a graph of a frequency curve plotted over incremental steps from 1 through 103. FIG. 4B is an associated table of the frequency steps from 1 through 100 with corresponding divisor, frequency, and delta values. The divisor is calculated by the following formula:

divisor=256−(n+92), where n is the incremental frequency step number.

The frequency is calculated from the following formula:

frequency=(5529600+(divisor×2))/divisor.

As can be seen in FIGS. 4A and 4B, the frequency curve is nonlinear. The nominal frequency initially used by the microprocessor to generate an acoustic energy wave can be selected from any one of the scale of frequencies. As shown in FIG. 4B, the scale of frequencies for this embodiment ranges from 33,719 hertz to 85,073 hertz, divided into 100 steps numbered 0–99. It is to be understood that the frequency curve and table in FIGS. 4A and 4B are specific to the disclosed transducers, and that adjustments may need to be made in the frequency curve to achieve optimal performance with other transducers, which can be determined empirically.

As an example, if the nominal frequency were initially 38,402 hertz, this would correspond to frequency increment number 20 in table 4B. The microprocessor initially generates acoustic energy waves at the nominal frequency and several measurements are made at the nominal frequency as shown in FIG. 3. The number of initial measurements at the nominal frequency can vary from 1 to however many are desired. Typically, several measurements are taken at the nominal frequency.

Next, the microprocessor adjusts the frequency upward by an incremental value, typically one incremental step. In the described example, the incremental value would be increased from 20 to 21. This results in a frequency change upward to 38,670.53 hertz. One measurement is then taken at this frequency, after which the microprocessor 12 changes the frequency back to the nominal frequency for several additional measurements.

The microprocessor 12 then reduces the nominal frequency by an incremental value of 1, which in this case is the frequency of 38,137.17 hertz in incremental step 19. It is to be understood, however, that the adjustment downward of the frequency can be made to any frequency from the table in FIG. 4B. In a preferred embodiment, the adjustment downward is at the same incremental change as the adjustment previously made upward.

After the measurement is taken at the reduced frequency, the microprocessor 12 then increases the frequency back to the nominal frequency for several further measurements. The microprocessor 12 then increases the nominal frequency by a multiple of the incremental value previously used for the first up and down adjustments. In the embodiment illustrated in FIG. 3, the incremental value is increased by 5. This results in an adjustment upward to frequency step number 25, which is associated with the frequency of 39,783.29 hertz. Finally, after several more measurements at the nominal frequency, the microprocessor 12 reduces the frequency, ideally by the same incremental change as it was previously increased, and an additional measurement taken.

The microprocessor 12 then scales all of the measurements to enable a direct comparison. At this point, if there is additional material to be measured on the object 23, the process repeats itself, and a loop counter is used to count the number of times the process is repeated. Ideally, the length of the object 23 and the speed at which the object 23 moves past the transducers determines the number of times the measurements are repeated. In a preferred embodiment, once the entire object moves past the transducers, the microprocessor 12 determines the frequency at which the highest measurable acoustic energy wave was received at the transmitter 18. This determined frequency is then used as the nominal frequency for the next object to be measured.

The present invention is adaptable for use in a manufacturing plant where multiple objects having the same physical size and shape are scanned and measured with the transducers, and the maximum acoustic energy is achieved by adjusting the frequency through the microprocessor instead of adjusting the distance from the transducers to the object.

The process of the present invention will repeat itself for every object that enters the system. The results of the measurements can be displayed in visual format on a computer screen, a printout, or both. For example, a graph can be generated showing the measurements of each transducer pair along the length of the object. In this way, anomalies in the interior of the object, such as delaminations, can be visually observed.

As will be readily appreciated from the foregoing, the disclosed embodiments of the present invention enable the finding of an optimal frequency to be utilized in acoustic sensing, such as ultrasonic examination. Because of the effect of temperature, humidity, and density on the wavelength of ultrasound waves, the present invention provides automatic continuous monitoring and adjustment of the frequency to maximize the received signal amplitude. In addition, while wear and tear on the fixturing also effects the length of the reverberation chamber, the method of the present invention maintains the frequency at the maximum value. Thus, the disclosed embodiments of the invention provide a self-calibrating ultrasonic tool that utilizes the reverberation chambers to maximize the single amplitude of a wave that travels through the air to the object, through the object, and finally through the air from the object. The present invention also magnifies the signal without introducing additional electrical noise in the system.

While preferred embodiments of the invention have been illustrated and described, it is to be understood that various changes may be made therein without departing from the spirit and scope of the invention. Hence, the invention is to be limited only by the scope of the claims that follow and the equivalents thereof.

What is claimed is:

1. An acoustic sensing method, comprising:

generating an initial acoustic energy wave at a nominal frequency, and generating successive acoustic energy waves through an object, each successive acoustic energy wave generated at a different frequency than the previous acoustic energy wave, wherein generating successive acoustic energy waves comprises adjusting the frequency both up and down by a first incremental value, then adjusting the frequency both up and down by a second incremental value;

sensing the initial and successive acoustic energy waves from the object and determining the frequency of the sensed acoustic energy wave having the highest energy level; and changing the nominal frequency to the determined frequency.

2. The method of claim 1 wherein the second incremental value is a multiple of the first incremental value.

3. The method of claim 1 wherein generating successive acoustic energy waves comprises adjusting a prior frequency to a successive frequency such that the successive frequency is equal to:

(5529600+2d)/d, where:

d=256−(n+92), and n=the incremental number of the successive frequency on a scale of frequencies.

4. An ultrasonic examination system for examining an object, comprising:

a microprocessor configured to generate frequency signals;

a first transducer coupled to the microprocessor and adapted to generate acoustic energy waves into the object in response to the frequency signals;

a second transducer coupled to the microprocessor and adapted to receive acoustic energy waves from the object and to generate corresponding acoustic energy signals, the microprocessor configured to adjust the frequency signal in response to the acoustic energy signals to the frequency signal associated with the highest acoustic energy signal; and wherein the microprocessor is configured to adjust a prior frequency to a successive frequency such that the successive frequency is equal to:

$$(5529600+2d)/d,$$

where:

$$d=256-(n+92),$$

and n=the incremental number of the successive frequency on a scale of frequencies.

5. The system of claim 4 wherein the processor is configured to generate a nominal frequency signal and successive frequency signals, each successive frequency signal generated at a different frequency than the previous frequency signal, the microprocessor further configured to adjust the nominal frequency signal to the frequency signal associated with the highest energy value signal.

6. The system of claim 4, further comprising a mounting apparatus adapted to hold the first and second transducers at a fixed distance from the object.

7. A method for acoustic sensing of an object in a computer-controlled system, comprising:

performing a plurality of acoustic energy measurements of the object at a nominal frequency and at different successive frequencies, including adjusting a prior frequency to a successive frequency such that the successive frequency is equal to:

$$(5529600+2d)/d,$$

where:

$$d=256-(n+92),$$

and n=the incremental number of the successive frequency on a scale of frequencies;

determining the frequency associated with the highest measured acoustic energy and changing the nominal frequency to the determined frequency; and repeatedly performing the plurality of acoustic measurements and determining the frequency associated with the highest measured acoustic energy.

8. A method for acoustic sensing of an object in a computer-controlled system, comprising:

performing a first acoustic measurement at a nominal frequency;

performing a second acoustic measurement at a second frequency that is increased from the nominal frequency by an incremental value;

performing a third measurement at the nominal frequency;

performing a fourth measurement at a third frequency that is reduced from the nominal frequency by the incremental value;

performing a fifth measurement at the nominal frequency;

performing a sixth measurement at a frequency that is increased by a second incremental value;

performing a seventh measurement at the nominal frequency;

performing an eighth measurement at a frequency that is reduced by the second incremental value;

determining the acoustic measurements having the highest acoustic energy; and changing the nominal frequency to the frequency associated with the acoustic measurement having the highest acoustic energy.

9. A method for acoustic sensing of an object in a computer-controlled system, comprising:

performing a first acoustic measurement at a nominal frequency;

performing a second acoustic measurement at a second frequency that is increased from the nominal frequency by an incremental value;

performing a third measurement at the nominal frequency;

performing a fourth measurement at a third frequency that is reduced from the nominal frequency by the first incremental value;

performing a fifth measurement at the nominal value;

performing a sixth measurement at a frequency that is increased by a second incremental value;

performing a seventh measurement at the nominal frequency;

performing an eighth measurement at a frequency that is reduced by the second incremental value;

repeating the first through the eighth measurements a predetermined number of times;

determining the acoustic measurements having the highest acoustic energy; and changing the nominal frequency to the frequency associated with the acoustic measurement having the highest acoustic energy.

10. An acoustic sensing method, comprising:

generating an initial acoustic energy wave at a nominal frequency and successive acoustic energy waves through an object, each successive acoustic energy wave generated at a different frequency than the previous acoustic energy wave by adjusting a prior frequency to a successive frequency such that the successive frequency is equal to:

$$(5529600+2d)/d,$$

where:

$$d=256-(n+92),$$

and n+the incremental number of the successive frequency on a scale of frequencies;

sensing the initial and successive acoustic energy waves from the object and determining the frequency of the sensed acoustic energy wave having the highest energy level; and changing the nominal frequency to the determined frequency.

* * * * *